US008968221B2

(12) United States Patent
Pryor et al.

(10) Patent No.: US 8,968,221 B2
(45) Date of Patent: Mar. 3, 2015

(54) APPARATUS AND METHODS FOR PHOTOTHERAPY

(75) Inventors: Brian Pryor, Ewing, NJ (US); Sean Xiaolu Wang, Wilmington, DE (US)

(73) Assignee: BWT Property, Inc., Newark, DE (US)

( * ) Notice: Subject to any disclaimer, the term of this patent is extended or adjusted under 35 U.S.C. 154(b) by 1491 days.

(21) Appl. No.: 12/104,012

(22) Filed: Apr. 16, 2008

(65) Prior Publication Data

US 2008/0262394 A1 Oct. 23, 2008

Related U.S. Application Data

(60) Provisional application No. 60/912,284, filed on Apr. 17, 2007.

(51) Int. Cl.
| | |
|---|---|
| *A61H 1/00* | (2006.01) |
| *A61H 1/02* | (2006.01) |
| *A61H 5/00* | (2006.01) |
| *A61H 15/00* | (2006.01) |
| *A61N 5/06* | (2006.01) |
| *A61H 7/00* | (2006.01) |
| *A61H 15/02* | (2006.01) |
| *A61N 5/067* | (2006.01) |

(52) U.S. Cl.
CPC .............. *A61N 5/0619* (2013.01); *A61H 7/007* (2013.01); *A61H 15/0092* (2013.01); *A61H 15/02* (2013.01); *A61H 2015/0064* (2013.01); *A61H 2201/10* (2013.01); *A61N 2005/063* (2013.01); *A61N 2005/0652* (2013.01); *A61N 2005/067* (2013.01); *A61H 2201/5028* (2013.01)

USPC ................ 601/19; 601/15; 601/113; 601/131

(58) Field of Classification Search
USPC ....... 607/88–95, 80; 601/15–20, DIG. 5, 112, 601/113, 131
See application file for complete search history.

(56) References Cited

U.S. PATENT DOCUMENTS

| | | | | |
|---|---|---|---|---|
| 1,844,247 | A * | 2/1932 | Freemon | 601/18 |
| 2,490,074 | A * | 12/1949 | Marty | 601/18 |
| 2,699,771 | A * | 1/1955 | Ruttger-Pelli | 601/15 |
| 5,336,159 | A * | 8/1994 | Cheng | 601/15 |
| 6,056,204 | A | 5/2000 | Glezer et al. | |
| 6,063,108 | A | 5/2000 | Salansky et al. | |
| 6,066,129 | A | 5/2000 | Larson | |
| 6,214,035 | B1 | 4/2001 | Streeter | |
| 6,413,268 | B1 | 7/2002 | Hartman | |
| 6,866,678 | B2 | 3/2005 | Shenderova et al. | |
| 7,033,382 | B2 | 4/2006 | Lach | |
| 7,083,580 | B2 * | 8/2006 | Bernabei | 601/15 |
| 7,144,247 | B2 | 12/2006 | Black | |

(Continued)

OTHER PUBLICATIONS

International Preliminary Report on Patentability and Written Opinion; Oct. 20, 2009; World Intellectual Property Organization (WIPO) (International Bureau of); PCT/US2008/060595; 6 pages.

(Continued)

*Primary Examiner* — Kristen Matter
(74) *Attorney, Agent, or Firm* — Fish & Richardson P.C.

(57) ABSTRACT

There is provided a phototherapy apparatus, in which the therapeutic light is delivered through or in proximity to one or more massage components. The massage component provides mechanical massage to the subject biological tissue and modifies the properties of the subject tissue in thickness, density, etc. to facilitate the absorption of the therapeutic light and enhance the effect of the phototherapy procedure.

8 Claims, 5 Drawing Sheets

(56) References Cited

U.S. PATENT DOCUMENTS

| | | | |
|---|---|---|---|
| 7,264,598 B2 * | 9/2007 | Shin | 601/15 |
| 7,282,037 B2 * | 10/2007 | Cho | 601/80 |
| 7,335,170 B2 * | 2/2008 | Milne et al. | 601/15 |
| 7,749,178 B2 * | 7/2010 | Imboden et al. | 601/15 |
| 7,762,964 B2 * | 7/2010 | Slatkine | 601/7 |
| 2003/0163068 A1 | 8/2003 | Kang | |
| 2003/0232303 A1 * | 12/2003 | Black | 433/29 |
| 2004/0138727 A1 | 7/2004 | Taboada et al. | |
| 2004/0193235 A1 | 9/2004 | Altshuler et al. | |
| 2004/0193236 A1 | 9/2004 | Altshuler et al. | |
| 2004/0236252 A1 | 11/2004 | Muzzi et al. | |
| 2004/0260209 A1 * | 12/2004 | Ella et al. | 601/7 |
| 2004/0260212 A1 | 12/2004 | Cho | |
| 2006/0235494 A1 | 10/2006 | Vanderschuit | |
| 2006/0253051 A1 | 11/2006 | Milne et al. | |
| 2007/0073366 A1 | 3/2007 | Porco | |
| 2007/0096118 A1 | 5/2007 | Mahalingam et al. | |
| 2008/0014011 A1 * | 1/2008 | Rossen | 401/195 |
| 2009/0001372 A1 | 1/2009 | Arik et al. | |
| 2009/0234253 A1 | 9/2009 | Vandenbelt et al. | |
| 2009/0299236 A1 | 12/2009 | Pryor et al. | |
| 2011/0144725 A1 | 6/2011 | Pryor et al. | |

OTHER PUBLICATIONS

International Search Report; Aug. 7, 2008; World Intellectual Property Organization (WIPO) (International Bureau of); PCT/US2008/060595; 3 pages.

* cited by examiner

# APPARATUS AND METHODS FOR PHOTOTHERAPY

REFERENCE TO RELATED APPLICATIONS

This application claims inventions which were disclosed in Provisional Patent Application Nos. 60/912,284, filed Apr. 17, 2007, entitled "Apparatus and Method for Improved Phototherapy;" 60/976,554, filed Oct. 1, 2007, entitled "Apparatus and Method for Improved Phototherapy;" and 60/983,719, filed Oct. 30, 2007, entitled "Apparatus and Method for Improved Phototherapy." The benefit under 35 USC §119(e) of the above mentioned U.S. Provisional Applications is hereby claimed, and the aforementioned applications are hereby incorporated herein by reference.

FIELD OF THE INVENTION

This invention relates to apparatus and methods for phototherapy.

BACKGROUND

Phototherapy relates to treatment of biological tissues, such as skin tissues, using visible, ultraviolet, and/or infrared lights. The light treatment may be applied solely for sterilization, pain relief, bio-modulation, and photo-rejuvenation. Alternatively, the treatment may be used in combination with certain photo-sensitive drugs or nutrition supplements. In comparison with laser surgery, the light intensity employed in phototherapy is much lower. Thus the light sources used in phototherapy are not limited to lasers but may include light emitting diodes (LEDs) and/or certain types of lamps as well. Typical applications of phototherapy include wound healing, cellulite reduction, skin rejuvenation, pain relief, fat reduction and contouring, laser acupuncture, pressure ulcer treatment, etc.

It is well known in the prior art that phototherapy may be applied in combination with other treatment methods such as local heating/cooling, magnetic therapy, mechanical massage involving rolling, kneading, vibrating components, etc. Some examples can be found in U.S. Pat. No. 7,033,382 to Lach; and U.S. Patent Application Nos. 20060253051 to Milne et al, 20060235494, 20040236252 to Muzzi et al, and 20070073366 to Porco. However, none of the prior art disclosure suggests to apply phototherapy with other treatment methods in a concerted manner, where phototherapy and some or all of the other treatment methods are applied to the same target area and benefit from each other thereby producing significantly improved therapeutic results.

SUMMARY OF THE INVENTION

There is provided a phototherapy apparatus, wherein the therapeutic light is delivered through or in proximity to one or more massage components. The massage component provides mechanical massage to a subject biological tissue and modifies the properties of the subject tissue in thickness, density, local pressure, micro-circulation, etc. to facilitate the absorption and interaction of the therapeutic light with the subject tissue and enhance the effect of the phototherapy procedure. Meanwhile, the therapeutic light in its interaction with the illuminated tissue also facilitates and enhances the effect of the mechanical massage.

A phototherapy apparatus for treatment of a biological tissue is provided. The phototherapy apparatus comprising: at least one light source to provide therapeutic light to be absorbed by the biological tissue to produce a first therapeutic effect; and at least one massage component to provide mechanical massage to the biological tissue to produce a second therapeutic effect. The therapeutic light and mechanical massage are applied to the biological tissue in a concerted manner. The mechanical massage modifies a plurality of properties or conditions of the biological tissue to facilitate absorption or interaction of the therapeutic light with the biological tissue to improve the first therapeutic effect. The therapeutic light modifies a plurality of properties or conditions of the biological tissue to improve the second therapeutic effect.

A method for making a phototherapy apparatus for treatment of a biological tissue is provided. The method comprising the steps of: providing at least one light source to provide therapeutic light to be absorbed by the biological tissue to produce a first therapeutic effect; and providing at least one massage component to provide mechanical massage to the biological tissue to produce a second therapeutic effect. The therapeutic light and mechanical massage are applied to the biological tissue in a concerted manner. The mechanical massage modifies a plurality of properties or conditions of the biological tissue to facilitate absorption or interaction of the therapeutic light with the biological tissue to improve the first therapeutic effect. The therapeutic light modifies a plurality of properties or conditions of the biological tissue to improve the second therapeutic effect.

A method for treatment of biological tissue with phototherapy is provided. The method comprising the steps of: providing at least one light source to provide therapeutic light to be absorbed by the biological tissue to produce a first therapeutic effect; and providing at least one massage component to provide mechanical massage to the biological tissue to produce a second therapeutic effect. The therapeutic light and mechanical massage are applied to the biological tissue in a concerted manner. The mechanical massage modifies a plurality of properties or conditions of the biological tissue to facilitate absorption or interaction of the therapeutic light with the biological tissue to improve the first therapeutic effect. The therapeutic light modifies a plurality of properties or conditions of the biological tissue to improve the second therapeutic effect.

BRIEF DESCRIPTION OF THE FIGURES

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1b illustrates the operation procedure of the phototherapy apparatus of FIG. 1a.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of method steps and apparatus components related to phototherapy. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Figure 1A:
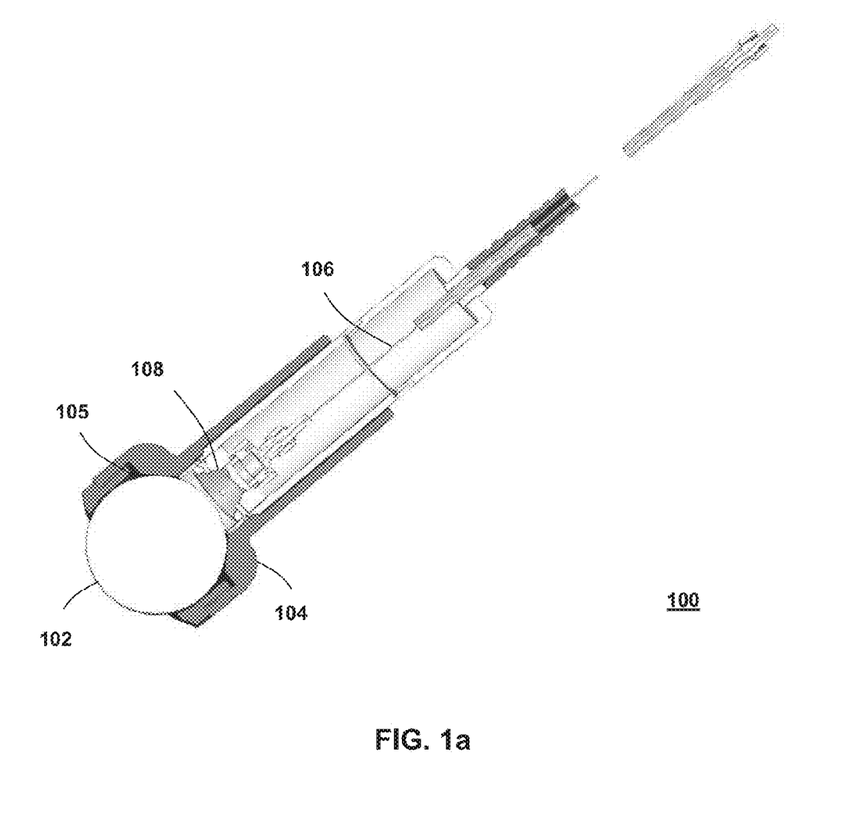
FIG. 1a illustrates one exemplified embodiment of the phototherapy apparatus, in which the therapeutic light is delivered through a transparent massage ball.

In the first embodiment of the present invention as shown in FIG. 1a, the phototherapy apparatus 100 comprises a rolling massage ball 102 coupled to a top of a hand piece 104. The massage ball 102 can rotate freely in all directions (a 360° freedom of movement) in a chamber 105 of the hand piece 104 with controlled friction. The therapeutic light emitted from a laser or a light emitting diode (LED) (both not shown) is first coupled into or carried by an optical fiber 106 and then delivered onto the massage ball 102 through a beam expander 108 wherein the therapeutic light beam is expended therefore. The massage ball 102 is transparent at the wavelength of the therapeutic light. Thus the subject therapeutic light will transmit through the massage ball 102 to the biological tissue for treatment purposes. In a slight variation of the embodiment, the therapeutic light can be delivered onto the massage ball via free space optics or other types of light guides all of which are contemplated by the present invention.

Figure 1B:
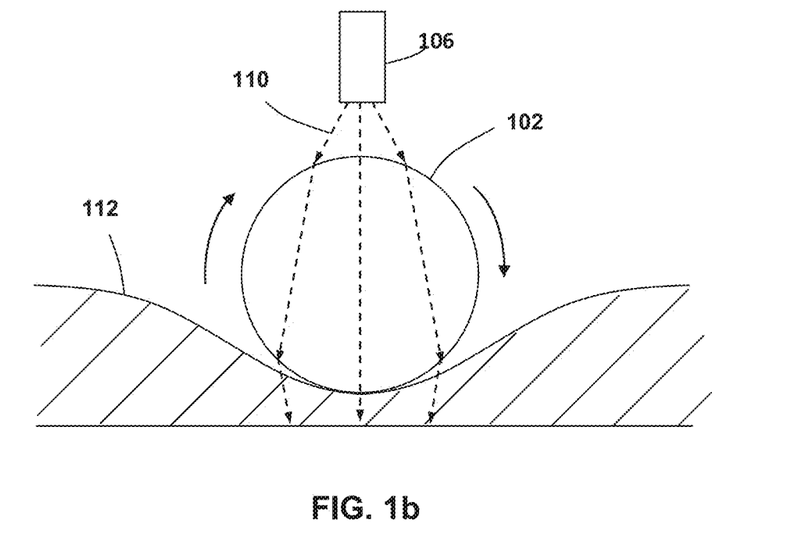

Referring now to FIG. 1b, the phototherapy apparatus 100 is utilized to treat a skin tissue 112, where the therapeutic light 110 is delivered through the transparent massage ball 102. When a force is applied onto the hand piece (not shown), the massage ball 102 will roll on the skin tissue 112 and deliver a pressure on the skin tissue in contact with the massage ball 102. On one hand, this rolling and kneading action causes an increase in blood circulation and fluid mobilization of the subcutaneous tissue, smoothes and firms the subject anatomy. Thus lipolysis is restored and fat cell metabolism is reactivated, resulting in the reduction of fat tissue and smoothing of cellulite. It also can help for the relief of muscle aches and pain. On the other hand, the action also causes a reduction in skin thickness and an increase in skin density. This change in skin tissue property helps to reduce the overall absorption and scattering loss of the therapeutic light 110 and allows the therapeutic light 110 to penetrate deeper under the skin and induce stronger photochemical processes, e.g. increase of ATP (adenosine triphosphate), triggering of photo neurological response and activation of enzymes, changes in local pressure, increases in temperature and permeability of cellular membranes. Since the massage ball 102 is in contact with the skin tissue 112, the therapeutic light 110 will penetrate into the skin tissue 112 directly with no air interface. This feature allows the practitioner to control the intensity of the delivered therapeutic light in a more accurate manner. The photo bio-modulation in turn helps to enhance the effect of the mechanical massage by stimulating inter or intra cellular response, increasing micro-circulation, etc.

Figure 2:
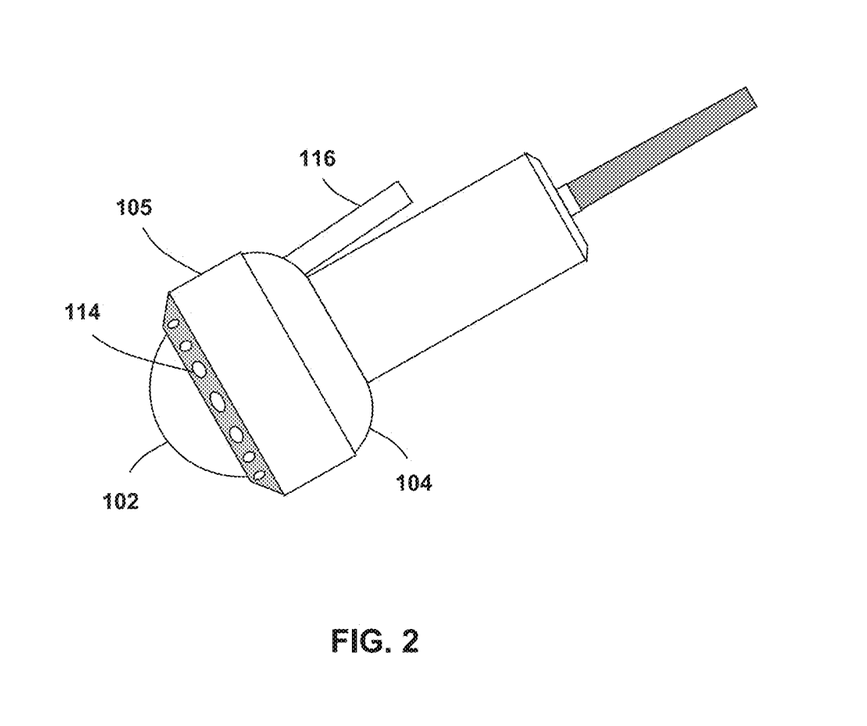
FIG. 2 illustrates a slight variation of the phototherapy apparatus of FIG. 1, in which liquid or air can be delivered around the massage ball through an array of holes.

In a slight variation of the present embodiment as shown in FIG. 2, the ball chamber 105 of the hand piece 104 comprises an array of holes 114 formed adjacent to the massage ball 102. Through these holes, cooling/warming air/liquid, or massage oil/lubricant with specific therapeutical effects may be delivered to the skin tissue during the treatment process. The cooling/warming air/liquid may be used for thermal therapy, while the massage oil/lubricant may help to soften/soothe the skin tissue and maintain its moisture level. The combined mechanical massage and photo bio-stimulation can enhance the response of the skin tissue to the massage oil/lubricant and allow same to penetrate deeper so as to be absorbed by inner skin tissues. The effect of such enhancements include, but are not limited to, increased micro-circulation, elevated temperature, and stimulated inter or intra cellular response. As another possibility, a gap can be introduced between the massage ball 102 and the chamber 105 for delivering cooling/warming air/liquid, or massage oil/lubricant to the subject tissue. The cooling/warming air/liquid, or massage oil/lubricant can be injected into the chamber 105 through a tube 116 connected to the hand piece 104.

Figure 7A:
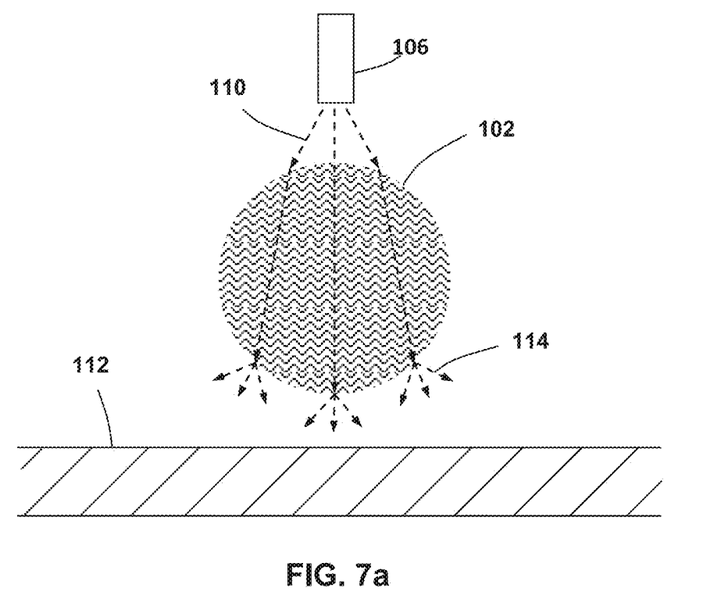
FIGS. 7a and 7b illustrate another variation of the phototherapy apparatus of FIG. 2, in which the massage ball has a diffusive or scattering optical surface.
Figure 7B:
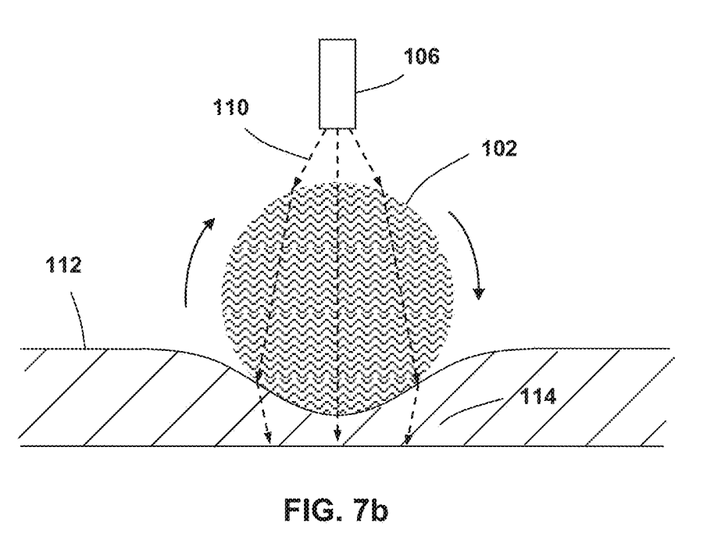

In another variation of the present embodiment as shown in FIG. 7a and FIG. 7b, the massage ball 102 may have a diffusive or scattering optical surface, which is capable of spreading the transmitted light into various angles and directions. The diffusive surface can be prepared by forming some type of micro-structures on the surface of the massage ball, or by coating a layer of diffusive optical material on the massage ball. Referring to FIG. 7a, when the massage ball 102 is not in contact with the skin tissue 112, the therapeutic light 110 is diffused by the diffusive surface as it transmits through the massage ball into air. Thus the transmitted light 114 has an increased spread angle and hence a reduced light intensity when viewed from a distance away. This reduction in viewed light intensity enhances the safety level of the phototherapy apparatus. In comparison, when the massage ball 102 is in contact with the skin tissue 112 as shown in FIG. 7b, the transmitted light 114 is much less distorted or spread. This is due to the fact that the skin in contact with the surface of the massage ball serves as an optical index matching medium which effectively reduces diffusing or scattering cause by the massage ball surface. Hence, the light beam is effectively delivered into the tissue with desired direction, angle, power density, depth, and intensity distribution. As another variation, certain optical index matching liquids, gels, suspension particles, powders may be applied between the massage ball 102 and the skin tissue 112 to further enhance light transmittance and reduce the light distortion caused by the massage ball surface. Those optical index matching media may also have therapeutic or pharmaceutical effect to further improve the effect of phototherapy.

In yet another variation of the present embodiment, the massage ball (or simply an optical window with curved surface) 102 is rigidly affixed to the chamber 105 and moves together or in unison with the hand piece 104. In this variation, the mechanical massage is performed by kneading the subject tissue 112 with the massage ball 102 without the rolling action.

In yet another variation of the present embodiment, a motor is installed in the hand piece 104 and mechanically coupled to massage ball 102 to generate rolling, kneading, and/or vibration movements of the massage ball 102.

One application of the phototherapy apparatus 100 is relieving the pain associated with migraine headaches, in which therapeutic light is delivered through the transparent massage ball to the forehead, temples, paranasal sinus, and/or neck of the patient. The optical properties of the massage ball, such as its refractive index, diameter or curvature, etc. can be utilized to shape the light beam to an ideal spot size or value. The phototherapy apparatus 100 may further comprise a touch sensor (not shown) or a pressure sensor (also not shown), such as a spring loaded device feature to control the on/off status of the light source in such a way that the light source can only be turned on when the massage ball touches the skin tissue. This helps to improve the safety of laser treatments around the eye by limiting the chance of laser exposure to the eye directly. Other applications of the phototherapy apparatus 100 comprise cellulite reduction, skin rejuvenation, pain relief, fat reduction and/or contouring, laser acupuncture, wound healing, and/or pressure ulcer treatment.

As can be seen, a variety of embodiments are possible within the scope of the present invention.

Figure 3:
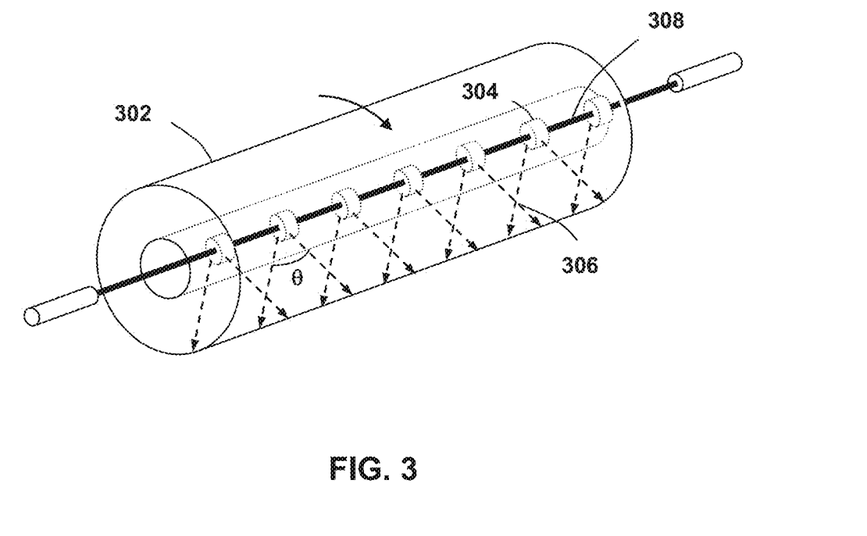
FIG. 3 illustrates a second exemplified embodiment of the phototherapy apparatus, in which the therapeutic light is delivered from inside of a transparent massage roller.

Referring to FIG. 3, the second embodiment of the phototherapy apparatus comprises a hollow massage roller 302 with an array of therapeutic laser diodes or LEDs 304 mounted along an inner axis 308 within the roller 302. Each of the laser diodes or LEDs 304 is designed to emit therapeutic light 306 with a predetermined divergence angle (θ) as shown in the figure. The roller 302 is made of material transparent to the wavelength of the therapeutic light 306. Correspondingly, when the roller 302 is applied to roll across a subject tissue surface to provide mechanical massage, the therapeutic light 306 simultaneously induce photo bio-modulation in the massaged tissue to produce enhanced phototherapy results.

Figure 4:
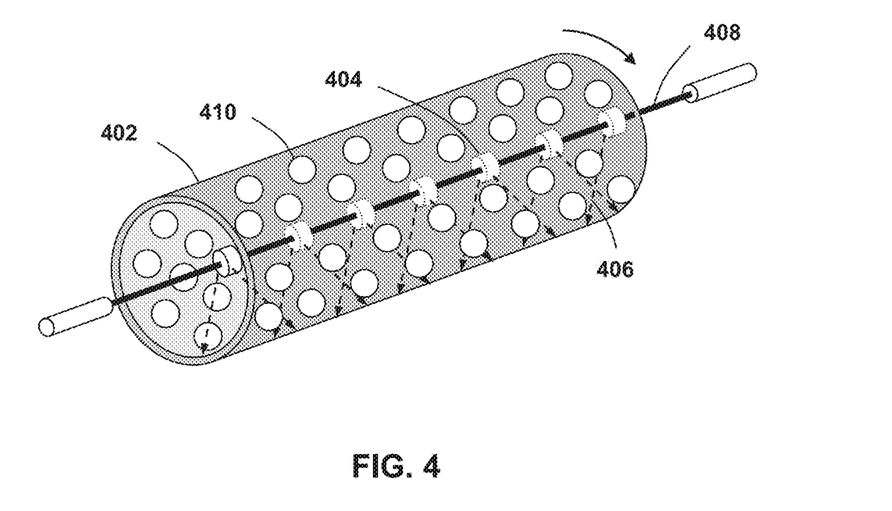
FIG. 4 illustrates a slight variation of the phototherapy apparatus of FIG. 3, in which the massage roller is made of non-transparent material comprising a matrix of holes.

In a slight variation of the present embodiment as shown in FIG. 4, the phototherapy apparatus comprises a hollow massage roller 402 made of material not transparent at the wavelength of the therapeutic light 406, where the therapeutic light 406 is produced by an array of therapeutic laser diodes or LEDs 404 mounted along the inner axis 408 of the massage roller 402. The massage roller 402 comprises a matrix of holes 410 which can let the therapeutic light 406 pass through to produce a patterned illumination onto the surface of the subject tissue. This kind of spatially modulated illumination pattern can further enhance the photo bio-modulation effect. In this embodiment, a positive or negative air pressure from a pressure source (not shown) may be applied through the matrix of holes as an added way to manipulate the treatment area. Either cooled or warm/hot air can be blown through the holes for decreasing or increasing the temperature of the skin. Alternatively, the massage roller 402 can be made of material transparent to the wavelength of the therapeutic light 406 except part of the roller surface is covered by patches of non-transparent materials to produce a patterned illumination.

Figure 5:
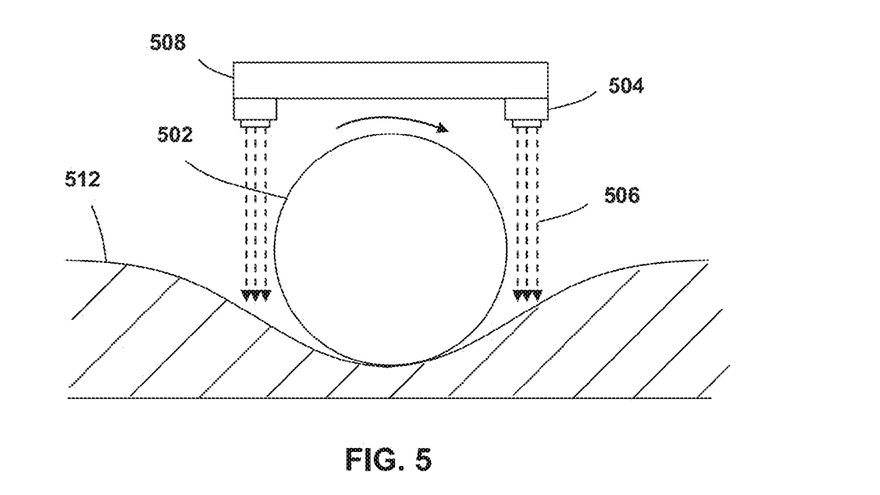
FIG. 5 illustrates a third exemplified embodiment of the phototherapy apparatus, in which the therapeutic light is delivered in proximity to a massage component.

In the third embodiment of the present invention as shown in FIG. 5, the therapeutic light sources 504 are mounted on a fixture 508 mechanically coupled to a massage component 502. The therapeutic light 506 produced by the light source 504 is delivered to the subject tissue 512 along a path proximal to the massage component 502. As the massage component 502 rolls across the tissue 512, the therapeutic light 506 induces photochemical reaction in the massaged tissue 512 before the tissue restores to its original state. Thus similar enhancement in phototherapy result is produced. In this embodiment, the massage component 502 needs not to be transparent to the therapeutic light 506.

Figure 6:
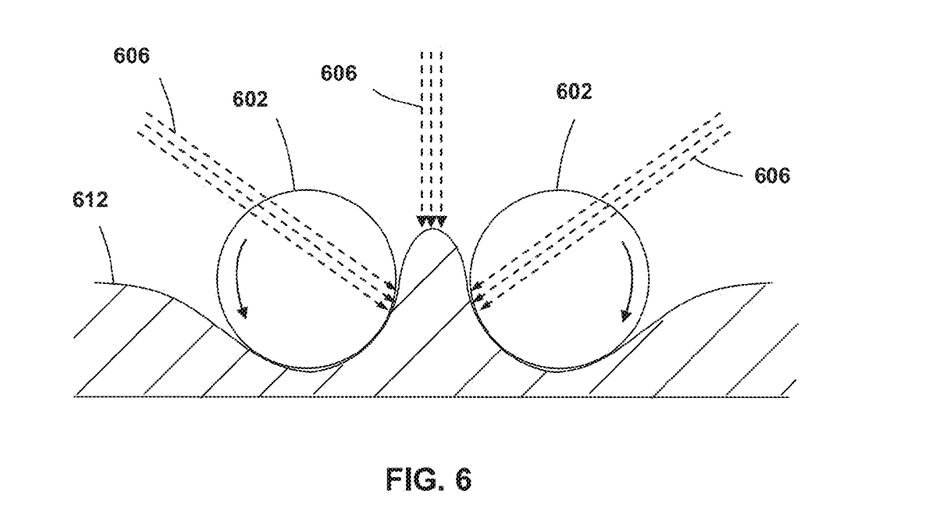
FIG. 6 illustrates a fourth exemplified embodiment of the phototherapy apparatus, in which the therapeutic light is delivered in proximity to two massage rollers rolling in opposite directions.

Referring to FIG. 6, the fourth embodiment of the phototherapy apparatus comprises two massage rollers 602 rolling in opposite directions, or with different rolling speeds or different surface frictions. Those rolling movements cause a portion of the tissue 612 between the two rollers 602 to be squeezed and therefore increasing in height. By illuminating the raised tissue with the therapeutic light 606, either through, or in proximity to the two rollers 602, the inner layer of the tissue, which is hard to reach when illuminated from top of the tissue, can be treated with the phototherapy procedure. The height of the raised tissue can be further increased by employing a vacuum sucker (not shown) on top of the rollers and mechanically coupled thereto.

The disclosed phototherapy apparatus can be used on animal subjects as well. For these veterinarian applications, a comb or comb-like component (not shown) can be integrated in front of the massage/phototherapy component to part the hair of the animal before massage/phototherapy treatment of the skin underneath is performed.

In the foregoing specification, specific embodiments of the present invention have been described. However, one of ordinary skill in the art appreciates that various modifications and changes can be made without departing from the scope of the present invention as set forth in the claims below. For example, the therapeutic light source and the massage component are not limited to the presently disclosed forms. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A phototherapy apparatus for treatment of a biological tissue, the phototherapy apparatus comprising:
   a hand piece;
   at least one light source that emits therapeutic light to be absorbed by the biological tissue to produce a first therapeutic effect;
   at least one rolling massage ball coupled within a chamber of the hand piece and transparent to the therapeutic light, wherein the at least one rolling massage ball can rotate in all directions so as to provide mechanical massage to the biological tissue to produce a second therapeutic effect;

an optical fiber that receives the therapeutic light emitted by the at least one light source and that carries the therapeutic light; and a beam expander coupled to the optical fiber and configured to transmit the therapeutic light carried by the optical fiber, the beam expander positioned external of and spaced apart from the at least one rolling massage ball such that the therapeutic light is delivered from the beam expander onto an outer surface of the at least one rolling massage ball and through the at least one rolling massage ball and such that the therapeutic light and the mechanical massage can be applied to the biological tissue in a concerted manner.

2. The phototherapy apparatus of claim 1, wherein the at least one rolling massage ball has a diffusive optical surface capable of increasing a spread angle of the therapeutic light.

3. The phototherapy apparatus of claim 1, wherein the at least one light source comprises a laser, a light emitting diode, or a lamp.

4. The phototherapy apparatus of claim 1, further comprising a touch sensor to monitor a contact/pressure between the at least one rolling massage ball massage and the biological tissue and to obtain a contact/pressure signal, wherein the contact/pressure signal is utilized to control the at least one light source.

5. The phototherapy apparatus of claim 1, further comprising a means for delivering fluid substance along the at least one rolling massage ball massage to improve said first and second therapeutic effect.

6. A method for treating a biological tissue with phototherapy, the method comprising the steps of:
   providing a phototherapy apparatus comprising:
      a hand piece;
      at least one light source that emits therapeutic light to be absorbed by the biological tissue to produce a first therapeutic effect;
      at least one rolling massage ball coupled within a chamber of the hand piece and transparent to the therapeutic light, wherein the at least one rolling massage ball can rotate in all directions so as to provide mechanical massage to the biological tissue to produce a second therapeutic effect;
   an optical fiber that receives the therapeutic light emitted by the at least one light source and that carries the therapeutic light; and
      a beam expander coupled to the optical fiber and configured to transmit the therapeutic light carried by the optical fiber, the beam expander positioned external of and spaced apart from the at least one rolling massage ball such that the therapeutic light is delivered through the at least one rolling massage ball and a refractive index and a diameter of the at least one rolling massage ball massage are controlled to shape the therapeutic light to a predetermined spot size,
   applying, using the phototherapy apparatus, said therapeutic light and mechanical massage to the biological tissue in a concerted manner, wherein the mechanical massage modifies a plurality of properties or conditions of the biological tissue to facilitate absorption or interaction of the therapeutic light with the biological tissue to improve said first therapeutic effect, and the therapeutic light modifies a plurality of properties or conditions of the biological tissue to improve said second therapeutic effect.

7. The method of claim 6, further comprising a step of providing a touch sensor to monitor the contact/pressure between the at least one rolling massage ball and the biological tissue and obtain a contact/pressure signal, wherein the contact/pressure signal is utilized to control the at least one light source.

8. The method of claim 6, further comprising a step of delivering fluid substance along the at least one rolling massage ball massage to improve said first and second therapeutic effect.

* * * * *

UNITED STATES PATENT AND TRADEMARK OFFICE
CERTIFICATE OF CORRECTION

Page 1 of 1

PATENT NO. : 8,968,221 B2
APPLICATION NO. : 12/104012
DATED : March 3, 2015
INVENTOR(S) : Brian Pryor and Sean Xiaolu Wang It is certified that error appears in the above-identified patent and that said Letters Patent is hereby corrected as shown below:

In the Claims

In column 7, line 22 of Claim 4, delete "ball massage" and insert -- ball --, therefor.

In column 7, line 28 of Claim 5, delete "ball massage" and insert -- ball --, therefor.

In column 8, line 15 (approximately) of Claim 6, delete "ball massage" and insert -- ball --, therefor.

In column 8, line 37 (approximately) of Claim 8, delete "ball massage" and insert -- ball --, therefor.

Signed and Sealed this
Fourteenth Day of July, 2015

Michelle K. Lee
*Director of the United States Patent and Trademark Office*